(12) United States Patent
Walsh et al.

(10) Patent No.: US 7,772,379 B2
(45) Date of Patent: *Aug. 10, 2010

(54) COMPOSITIONS AND PROCESSES FOR PREPARING 13-DEOXY-ANTHRACYCLINES

(75) Inventors: Gerald M. Walsh, Birmingham, AL (US); Richard D. Olson, Nampa, ID (US)

(73) Assignee: Gem Pharmaceuticals, LLC, Birmingham, AL (US)

( * ) Notice: Subject to any disclaimer, the term of this patent is extended or adjusted under 35 U.S.C. 154(b) by 53 days.

This patent is subject to a terminal disclaimer.

(21) Appl. No.: 11/777,057

(22) Filed: Jul. 12, 2007

(65) Prior Publication Data

US 2008/0015345 A1 Jan. 17, 2008

Related U.S. Application Data

(63) Continuation of application No. 10/982,873, filed on Nov. 8, 2004, now Pat. No. 7,244,829.

(51) Int. Cl.
*C07H 15/24* (2006.01)

(52) U.S. Cl. .................................................. 536/6.4

(58) Field of Classification Search ................... 536/6.4
See application file for complete search history.

(56) References Cited

U.S. PATENT DOCUMENTS

| 5,942,605 A | 8/1999 | Zhang et al. |
| 5,948,896 A | 9/1999 | Zhang |

OTHER PUBLICATIONS

Adriamycin Analogues. 2. Synthesis of 13-Deoxyanthracyclines by Thomas Smith et al., *Journal of Medicinal Chemistry*, 1978, vol. 21, No. 3.

*Primary Examiner*—Elli Peselev
(74) *Attorney, Agent, or Firm*—DLA Piper LLP (US)

(57) ABSTRACT

13-benzenesulfonylhydrazone anthracyclines useful in producing improved yields in the synthesis 13-deoxyanthrcyclines, and an improved method of reducing 13-benzenesulfonylhydrazone anthracyclines to 13-deoxyanthrcyclines wherein the reduction reaction is maintained at temperatures of about 55° C. to 64° C. without stirring or agitation. The reaction is completed with the addition of aqueous bicarbonate which forms the 13-deoxyanthracycline and precipitates. The precipitates are filtered and the precipitate and filtrate are extracted separately with organic solvents. The crude 13-deoxy anthracycline can be converted to 5-imino-13-deoxy anthracycline by reaction with methanolic ammonia. The reaction can also be performed with an acidic pyridinium salt instead of a strong acid so that neutralization of the reaction or extraction of the product is not necessary, thereby facilitating purification.

12 Claims, No Drawings

COMPOSITIONS AND PROCESSES FOR PREPARING 13-DEOXY-ANTHRACYCLINES

CROSS-REFERENCE TO RELATED APPLICATIONS

This application is a continuation application of and claims the priority benefit under 35 U.S.C. §120 of U.S. application Ser. No. 10/982,873 filed Nov. 8, 2004, titled: "COMPOSITIONS AND PROCESSES FOR PREPARING 13-DEOXY-ANTHRACYCLINES," now U.S. Pat. No. 7,244,829.

TECHNICAL FIELD

The present disclosure relates to compositions and processes for preparing 13-deoxy anthracyclines, and, more particularly, to the use of 13-benzenesulfonylhydrazone anthracycline intermediates for the synthesis and isolation of 13-deoxyanthracyclines, and to methods for preparing 13-benzenesulfonylhydrazone anthracyclines. The present disclosure is also related to novel 13-benzenesulfonylhydrazone intermediates and processes for preparing these intermediates.

BACKGROUND

The most well-known anthracycline anticancer drugs are doxorubicin and daunorubicin, which contain a 13-keto group. Doxorubicin, disclosed in U.S. Pat. No. 3,590,028, has a wide spectrum of anticancer utility and is used in the treatment of leukemias, lymphomas, and solid tumors. Daunorubicin, disclosed in U.S. Pat. No. 3,616,242, is useful in the treatment of acute leukemias. However, the utility of these drugs is limited by a serious side effect of cardiotoxicity so that the total amount of drug that can be given to a patient cannot exceed 550 mg/M$^2$ (E. A. Lefrak et al., Cancer, 32:302, 1973). Even at or near the recommended maximum total cumulative dosage (430-650 mg/M$^2$) significant and persistent heart dysfunction occurs in 60% of patients and 14% develop congestive heart failure. (A. Dresdale et al., Cancer, 52:51, 1983). Thus, while these drugs are useful to inhibit the growth of cancerous tumors, the patient may die of congestive heart failure because of the severe cardiotoxic side effect of the drugs.

It has also been found that the cardiotoxicity of these anthracyclines is produced by the metabolic reduction of the 13-keto moiety to a 13-dihydro alcohol metabolite (P. S. Mushlin et al., Fed. Proc., 45:809, 1986). In test systems where doxorubicin is not metabolized appreciably to the 13-dihydro alcohol metabolite(doxorubicinol) no significant cardiotoxic effects are observed (P. S. Mushlin et al., Fed. Proc., 44:1274, 1985; R. D. Olson et al., Fed. Proc., 45:809, 1986). In contrast, the 13-dihydro metabolites, doxorubicinol and daunorubicinol, produce cardiotoxicity in these same test systems at relatively low concentrations (1-2 micrograms/ml, R. D. Olson et al., Proceed. Am. Assoc. Cancer Res., 26:227, 1985; R. D. Olson et al., Proceed Am. Assoc. Cancer Res. 28:441, 1987).

If doxorubicin is allowed to remain in the test systems even for short periods of time some metabolic conversion occurs and the 13-dihydro metabolite is formed in sufficient quantity so that cardiotoxicity begins to develop (L. Rossini et al., Arch. Toxicol. Suppl., 9:474, 1986; M. Del Tocca et al., Pharmacol. Res. Commun., 17:1073, 1985). Substantial evidence has, thus, accumulated that the cardiotoxicity of drugs such as doxorubicin and daunorubicin results from the potent cardiotoxic effects produced by their 13-dihydro metabolites (P. Mushlin et al., FASEB Journal, 2:A1133, 1988; R. Boucek et al., J. Biol. Chem., 262:15851, 1987; and R. Olson et al., Proc. Natl. Acad. Sci., 85:3585, 1988).

More recently it has been discovered that the 13-deoxy forms of doxorubicin, daunorubicin, or other similar anthracyclines will not be metabolically converted to cardiotoxic 13-dihydro forms, and that the 5-keto group can be modified to a form that will be less likely to generate free radicals, thus providing additional improved safety. In particular, see WO99/08687, U.S. Pat. Nos. 5,984,896 and 5,942,605 and PCT/US99/04704, disclosures of which are incorporated herein by reference.

The first documented process for preparing certain 13-deoxy anthracyclines from 13-p-methylbenzenesulfonylhydrazone anthracyclines had relatively low yields, on the order of about 10% (see Smith, et al., J. Med. Chem. 1978 21, 280-283). Improved processes for synthesizing 13-deoxy anthracyclines from 13-p-methylbenzene-sulfonylhydrazone anthracyclines exhibiting enhanced yields are disclosed in WO99/08687 and U.S. Pat. No. 5,984,896. However, these processes employ a relatively large excess of reagents and take a relatively long time to carry out. Moreover, the yields, although increased, are less than optimum for commercial production. Furthermore, the use of 13-p-methylbenzene-sulfonylhydrazone anthracyclines results in about 3% or more of this starting material in the 13-deoxy anthracycline product. The use of 13-p-F-benzenesulfonylhydrazone anthracyclines is known, but the synthesis of 13-p-F—, 13-p-Cl—, or 13-p-nitrobenzenesulfonylhydrazone anthracyclines from their parent 13-keto anthracyclines produce lower yields compared to 13-p-methylbenzene-sulfonylhydrazone anthracyclines, and also produce lower yields of 13-deoxy anthracyclines.

SUMMARY

The compositions and processes of the present disclosure provide increased yield and purity of 13-doxy anthracyclines from corresponding 13-keto anthracyclines. One aspect of the present disclosure relates to compounds represented by the formula:

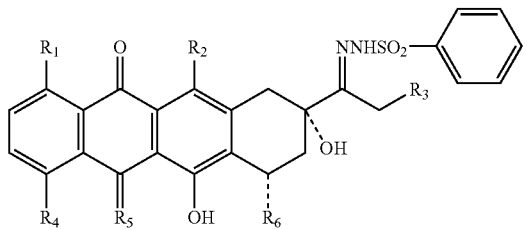

Wherein
R$_1$, R$_2$ and R$_3$ are H or OH;
R$_4$ is H, OH, alkyl, or O-alkyl;
R$_5$ is O or NH; and
R$_6$ is H, OH, or a sugar moiety.

The present disclosure also relates to a method for preparing a 13-benzenesulfonylhydrazone anthracycline as disclosed above, which comprises reacting a 13-keto anthracycline, or acid salt thereof, with benzenesulfonyl hydrazide in an alcohol solution.

A still further aspect of the present disclosure relates to a process for preparing 13-deoxyanthracycline (13-methylene anthracycline) derivatives from 13-benzenesulfonylhydrazone anthracyclines, which comprises:
1. Forming a reaction mixture by combining a 13-benzenesulfonylhydrazone anthracycline with a reducing agent such as sodium cyanoborohydride (NaCNBH) and a strong acid such as para-toluenesulfonic acid (PTSA) in an alcohol such as methanol.
2. Heating the reaction mixture without stirring or agitation
3. Neutralizing the reaction mixture with an aqueous base such as sodium bicarbonate in water ($NaHCO_3$), and thereby forming the 13-deoxy anthracycline product, and precipitating salts in the reaction mixture.
4. Filtering the precipitated salts from the reaction mixture, extracting the product from the precipitated salts with organic solvent, and extracting the product from the filtrate with organic solvent.

A still further aspect of the present disclosure relates to a process for preparing 5-imino-13-deoxyanthracycline derivatives from 13-deoxy anthracyclines by subjecting the 13-deoxyanthracycline to methanolic ammonia.

The present disclosure makes possible the complete reduction of the 13-benzenesulfonylhydrazone anthracycline to the corresponding 13-deoxyanthracycline.

According to the present disclosure, the 13-deoxy anthracycline can be isolated in a relatively simple manner.

The present disclosure makes it possible to produce 5-imino-13-deoxy anthracyclines from the crude 13-deoxy products.

The present disclosure makes it possible to synthesize the benzenesulfonylhydrazone anthracycline in 16 to 20 hours.

According to the present disclosure the 5-imino analogs can be synthesized from the crude 13-deoxy anthracycline product using methanolic ammonia without the need to protect the sugar amine group.

It has been found according to the present disclosure that an acidic pyridinium salt can be used in place of the strong acid to promote the reduction of the starting material, so that the reaction does not need to be neutralized or extracted, thereby facilitating purification of the product by preparative HPLC.

DETAILED DESCRIPTION OF THE PREFERRED EMBODIMENTS

While the following description details the preferred embodiments, it is to be understood that the disclosure is not limited in its application to the details of construction and arrangement of the parts illustrated in the accompanying drawings, since the disclosure is capable of other embodiments and of being practiced in various ways.

One embodiment relates to compounds represented by the formula:

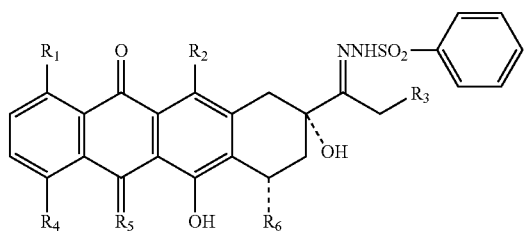

Wherein each $R_1$, $R_2$, and $R_3$ individually is H or OH;
$R_4$ is selected from the group consisting of H, OH, alkyl, and O-alkyl;
$R_5$ is O or NH;
$R_6$ is selected from the group consisting of H, OH, or a sugar.

The alkyl group typically contains 1 to 5 carbon atoms and more typically 1 to 3 carbon atoms.

The O-alkyl group typically contains 1 to 5 carbon atoms and more typically 1 to 3 carbon atoms; and $R_4$ is typically OCH3.

The above compounds are precursors for producing 13-deoxy anthracyclines compounds and 5-imino-13-deoxy anthracyclines derivatives which are useful as anticancer drugs. Examples of anthracycline compounds employed in the process of the present disclosure are doxorubicin, daunorubicin, carminomycin, epirubicin, idarubicin, and annamycin, with doxorubicin and daunorubicin being preferred.

13-keto anthracyclines can be converted to 13-deoxy anthracyclines by first converting the 13-keto anthracycline to a 13-para-substituted benzenesulfonylhydrazone anthracycline. The 13-para-substituted benzenesulfonylhydrazone anthracyclines that are known to be useful as starting materials in the synthesis of 13-deoxy anthracyclines are 13-p-methylbenzene-sulfonylhydrazone anthracycline, and 13-p-F-benzenesulfonylhydrazone anthracycline. Examples are 13-p-methylbenzenesulfonylhydrazone doxorubicin (I) and 13-p-F-benzenesulfonylhydrazone doxorubicin (II):

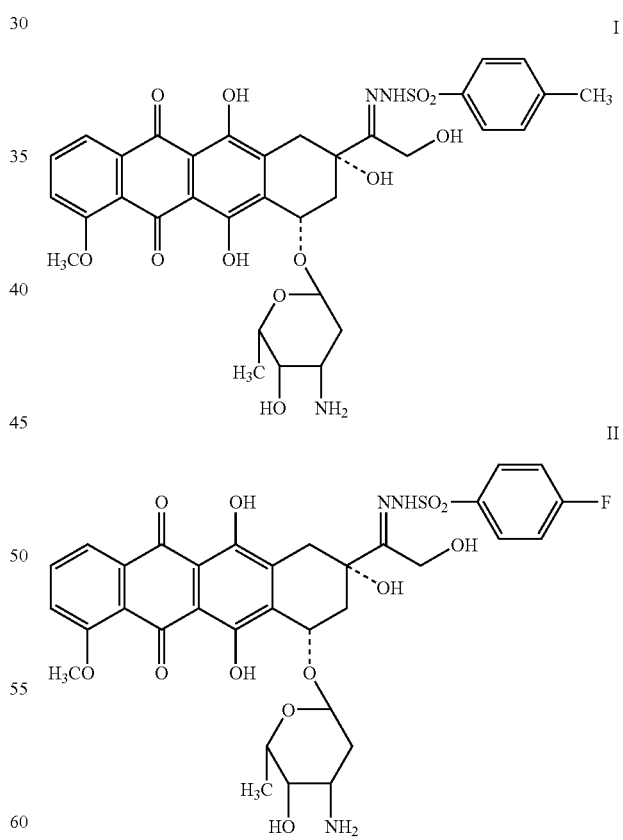

Compound I has an electron donating group on the benzene ring of the 13-p-methylbenzenesulfonylhydrazone moiety and is not completely reduced to the 13-deoxydoxorubicin product in the reduction reaction. Compound I is difficult to separate from the 13-deoxydoxorubicin product, and both silica column chromatography and preparative HPLC are required to purify the 13-deoxydoxorubicin product produced from Compound I.

Compound II has an electron withdrawing group on the benzene ring of the 13-p-F-benzenesulfonylhydrazone moiety and is completely reduced to the 13-deoxydoxorubicin product in the reduction reaction of the present invention. However, the synthesis of compound II from doxorubicin and p-F-benzenesulfonylhydrazine produces lower yields compared to the synthesis of compound I. In addition, the solubility of compound II in methanol is relatively poor, and compound II may take several hours to dissolve, depending on the temperature and desired concentration. This is also the case with p-Cl and p-nitro analogs. At temperatures below 20° C. compound II in methanol becomes gelatinous, preventing the processing of reaction solutions below 20° C. The yields of the 13-deoxydoxorubicin product from compound II are, consequently, reduced. Other examples include, for example, the 13-p-substituted benzene-sulfonylhydrazone analogs of daunorubicin, epirubicin, idarubicin, annamycin, and carminomycin.

13-p-substituted benzenesulfonylhydrazone anthracyclines are synthesized by combining the p-substituted benzenesulfonylhydrazine with a 13-keto anthracycline in alcohol and letting the solution stand at room temperature for 5 days. In our search for a more effective starting material for the synthesis of 13-deoxy anthracyclines we

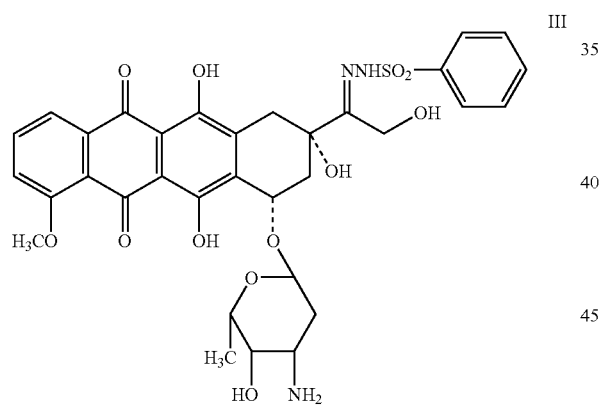

discovered that 13-benzenesulfonylhydrazonedoxorubicin (compound III) with no para substitution on the benzene ring was, surprisingly, devoid of the problems associated with p-substituted benzenesulfonylhydrazone anthracyclines such as compounds I and II. In addition, we further discovered that 13-benzene- (or p-substituted 13-benzene-)sulfonylhydrazone anthracyclines could be synthesized in 10 to 24 hours in methanol at about 35-60° C., preferably about 40-45° C., with yields and purity equal to that obtained from performing the reaction at room temperature for 5 days. The reaction of benzenesulfonylhydrazine with doxorubicin (IV) to give compound III, followed by reduction to the 13-deoxydoxorubicin product (compound V) is shown below:

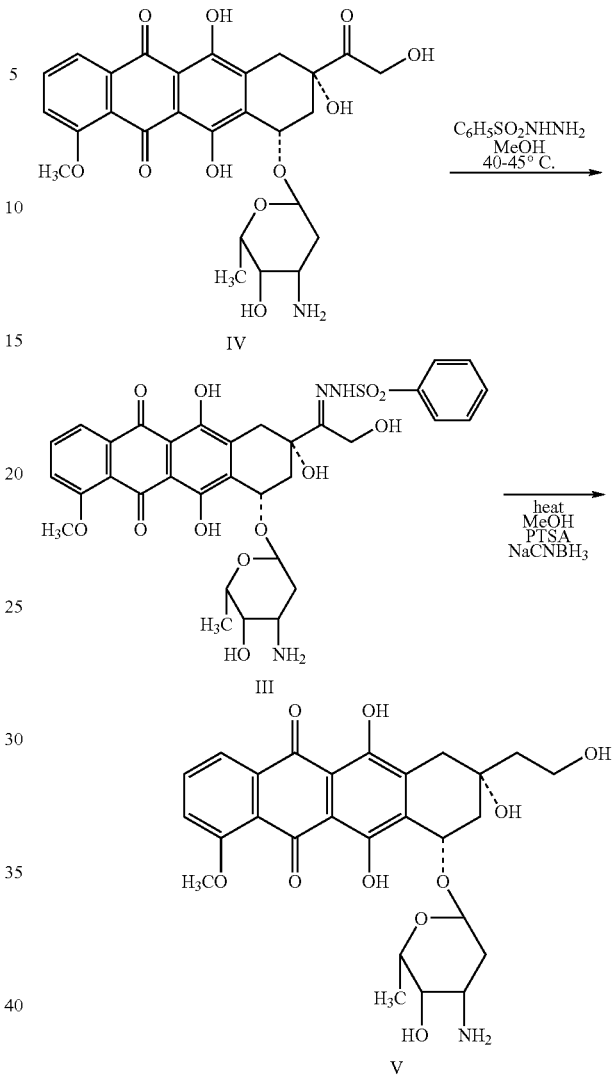

13-p-substituted benzenesulfonylhydrazone anthracyclines are converted to 13-deoxy anthracyclines by forming a reaction mixture of a 13-p-substituted benzene-sulfonylhydrazone anthracycline with a reducing agent and a strong acid, in many cases cyanoborohydride and p-toluene sulfonic acid (PTSA) in methanol. Presumably, the hydrazone is reduced by accepting a hydrogen from the acid and a hydrogen from the cyanoborohydride. However, the acid can also neutralize the cyanoborohydride, so the concentrations of the reactants and the temperature of the reaction appear somewhat important for optimum production of the 13-deoxy anthracycline product. It is generally accepted that the reaction mixture in methanol be heated so that the mixture refluxes, and that the reaction mixture be stirred. At the end of the reaction, the mixture is neutralized with the addition of aqueous base, which neutralizes the strong acid and cleaves the reduced hydrazine from the 13 position, leaving a methylene group in the 13 position.

Addition of aqueous base to the reaction mixture also produces the precipitation of salts which bind the 13-deoxy anthracycline product. The binding of product to the precipitated salts has required complex procedures to recover the product, such as acid extraction and multiple separations with silica gel and HPLC chromatography. We observed that any agitation of the reaction mixture during heating promotes excessive neutralization of the cyanoborohydride by the acid (PTSA), followed by excessive cleavage of the sugar from the anthracycline, reducing overall yield of the product. We further discovered that combining the reagents without stirring or agitation, and heating the reaction mixture without agitation or stirring produced substantially higher yields. The optimum temperature was found to be between 55 to 64° C., without stirring or agitation. We also discovered that the 13-deoxy anthracycline product can be readily removed from the precipitated salts by filtering the reaction mixture after adding the aqueous base, and then washing the salt residue with organic solvents such as a mixture of chloroform and methanol. The process is outlined below. Starting material, such as, for example, compound III, and sodium cyanoborohydride are dissolved in dry methanol and the temperature of the reaction mixture is reduced to 0 to 4° C. PTSA is dissolved in dry methanol and added to the cold reaction mixture. The reaction mixture is then heated between 55 and 64° C., preferably 59-60° C., for 1 to 4 hours, preferably for 2 hours, without stirring or agitation. The reaction mixture is then cooled, preferably to 0° C. or less and then cold (0 to 10° C.) bicarbonate saturated water is added to the cold reaction mixture to neutralize the acids and to form the product, compound V. Salts precipitate in the mixture of water and methanol, and the mixture of water and

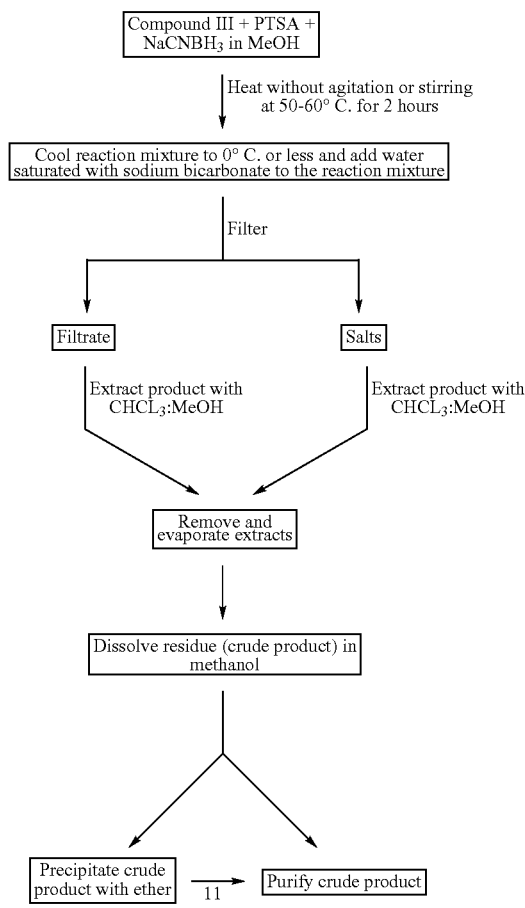

methanol is filtered under vacuum using a Buchner funnel and a vacuum flask. The salts on the filter paper in the Buchner funnel are washed with about 3.5:1 $CHCl_3$:methanol under vacuum thereby extracting the product, compound V, adhering to the salts. This extract can be collected into the same vacuum flask as the bicarbonate water/methanol mixture, or can be collected separately into a separate vacuum flask. Sufficient $CHCl_3$ is added to the flask containing the bicarbonate water/methanol mixture to create about a 3.5:1 mixture of chloroform and methanol. The product, compound V, is then extracted from the bicarbonate water into the chloroform/methanol. The organic extracts are separated from the water and evaporated to dryness. The residue, containing the product, compound V, is dissolved in methanol. Compound V, can be purified by chromatography procedures known in the art, or can be precipitated by the addition of ether.

It is generally known that 5-imino anthracyclines can be formed from 5-keto anthracyclines by reacting the 5-keto anthracyclines in cold methanolic ammonia. It is further known that 13-keto-14-OH anthracyclines require protection of the amine group in the sugar. 5-imino analogs of 13-deoxy anthracyclines can also be readily formed by reaction with cold methanolic ammonia, but we discovered that protection of the sugar amine is not required. In the present disclosure, crude 13-deoxy anthracycline product can be dissolved in methanolic ammonia and maintained at less than about 20° C., preferably about 0-4° C. until the reaction is complete, usually 1 to 5 days. The 5-imino analogs of the 13-deoxy anthracyclines can be formed prior to forming the HCl salt of the 13-deoxy compounds or afterwards, and before or after purification or precipitation. 5-imino-13-deoxy anthracyclines can be readily purified by chromatography methods well known in the art. An example of a 5-imino-13-deoxy anthracycline, 5-imino-13-deoxydoxorubicin (VIII), is shown below.

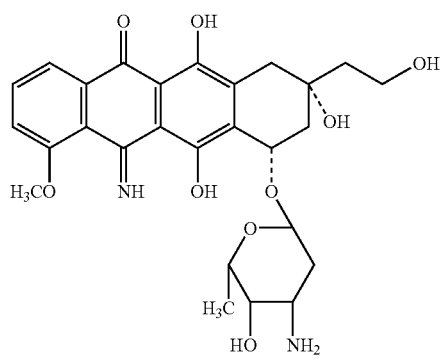

EXAMPLE 1

Preparation of 13-benzenesulfonylhydrazonedoxorubicin HCl (III)

The synthesis of compound III was compared to the synthesis of compounds I and II and to 13-p-methoxybenzenesulfonylhydrazonedoxorubicin (VI) and 13-p-nitrobenzenesulfonylhydrazonedoxorubicin (VII). 375 mg of the corresponding benzene- or p-substituted benzenesulfonylhydrazine and 500 mg of doxorubicin HCl (IV) were dissolved in 15 ml of anhydrous methanol. The solutions were heated at 40-45° C. for about 16-20 hours, or were maintained at room temperature (about 23-28° C.) for about 5 days, or were cooled at about 0-4° C. for about 10 days. At the end of the reaction 100 ml of diethyl ether were added to the methanol reaction mixtures to precipitate the products. The precipitates were washed with diethyl ether to remove methanol, and the precipitates were then dried in a dessicator under vacuum. The products were recovered in 90% or greater purity, measured by HPLC. The yields, based upon doxorubicin HCl (IV), were as follows:

| Compound | Yield (%) |
|---|---|
| 0 to 4° C. | |
| III | 96 |
| I | 91 |
| II | 62 |
| VI | 96 |
| 22-27° C. | |
| III | 96 |
| I | 98 |
| II | 86 |
| VI | 91 |
| 40-45° C. | |
| III | 98 |
| II | 88 |
| VII | 94 |

Compound III provided consistently high yields regardless of the temperature of the reaction, compared to compound II which provided consistently relatively poor yields. The results show that the synthesis can be performed at 40-45° C. for a shorter duration with yields equally good as those obtained at at lower temperatures for a longer duration.

Compound III:
  Mass Spectrum:
  Performed on an Aligent Ion Trap Mass Spectrophotometer (EN 824) (ESI positive ionization).
  Structure:

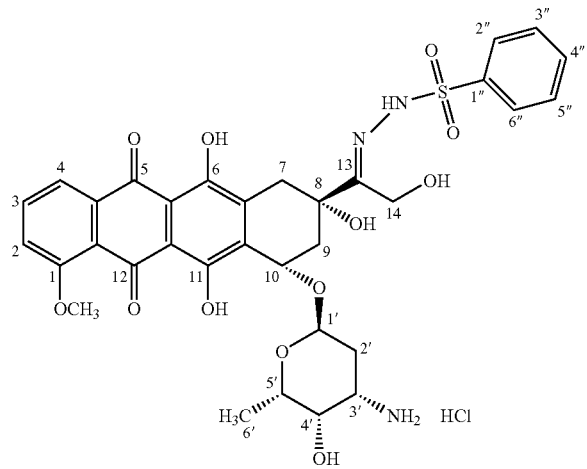

Formula: $C_{33}H_{36}N_3O_{12}S$

Molecular weight: 697.7 as the free base; 734.2 as the HCl salt

UV:
  Performed on an Aligent Technologies 8453 UV/Vis spectrophotometer (EN-246). Sample was prepared in methanol.

| $\lambda_{max}$ |
|---|
| $\lambda_{max}$ = 234 nm ($\epsilon$ = 31,737) |
| $\lambda_{max}$ = 251 nm ($\epsilon$ = 22,394) |
| $\lambda_{max}$ = 292 nm ($\epsilon$ = 4,492) |
| $\lambda_{max}$ = 497 nm ($\epsilon$ = 10,284) |

$^1$H NMR (300 MHz, DMSO-d6, $\delta$):
Performed on a Varian Mercury 300. Shifts are downfield from TMS (tetramethylsilane).

| $\delta$, ppm | Assignment |
|---|---|
| 1.15 | d, 3H, J = 6.3, 6'-CH$_3$ |
| 1.68 | dd, 1H, J = 12.7, 3.2, 2'-CH$_2$ |
| 1.90 | dt, 1H, J = 12.2, 3.7, 2'-CH$_2$ |
| 2.05 | m, 1H, 9-CH$_2$ |
| 2.34 | m, 1H, 9-CH$_2$ |
| 2.68 | d, 1H, J = 17.7, 7-CH$_2$ |
| 3.14 | d, 1H, J = 17.7, 7-CH$_2$ |
| 3.32 | m, 1H, 3'-H |
| 3.53 | m, 1H, 4'-H |
| 4.01 | s, 3H, 1-OCH$_3$ |
| 4.03 | m, 1H, 5'-H |
| 4.29 | s, 2H, 14-CH$_2$ |
| 4.98 | t, 1H, J = 6.3, 10-H |
| 5.30 | m, 1H, 1'-H |
| 5.38 | s, 1H, 8-OH |
| 5.45 | d, 1H, J = 6.3, 4'-OH |
| 5.62 | br s, 1H, 14-OH |
| 7.48 | m, 3H, 3"-H, 4"-H & 5"-H |
| 7.69 | t, 1H, J = 4.8, 3-H |
| 7.73 | d, 2H, J = 7.2, 2"-H & 6"-H |
| 7.81 | br s, 2H, 3'-NH$_2$ |
| 7.94 | d, 2H, J = 5.1, 2-H &4-H |
| 10.51 | br s, 2H, PhSO$_2$—HN—N=R |
| 13.30 | s, 1H, 6-OH or 11-OH |
| 14.01 | s, 1H, 6-OH or 11-OH |

EXAMPLE 2

Preparation of 13-deoxydoxorubicin HCl (V) from 13-benzenesulfonylhydrazonedoxorubicin HCl (III)

Compound V was synthesized from compound III, where compound III was synthesized at 23-27° C. (RT), 0-4° C. (cold) or 40-45° C. (hot). Compound V was also synthesized from compound II under similar conditions for comparison. 100 mg of compound III (or compound II) was dissolved in 6 ml dry methanol with 100 mg of NaCNBH$_3$. The reaction mixture was placed in an ice bath. 275 mg of PTSA was dissolved in 2 ml dry methanol and was then added to the cold reaction mixture without stirring or agitation, providing a total of 8 ml methanol. The reaction mixture was then heated at 59-60° C. for 2 hours without stirring or agitation. At the end of 2 hours the reaction mixture was placed in a freezer until the temperature of the reaction mixture was at or below 0° C. 12 ml of water saturated with sodium bicarbonate and at a temperature of 1-4° C. was then added to the cold 8 ml methanol reaction mixture. The water/methanol mixture was filtered in a Buchner funnel into a vacuum flask. The salts on the filter paper in the Buchner funnel were washed under vacuum with 20-40 ml of 3.5:1 chloroform:methanol to extract the product from the salts into the vacuum flask containing the filtrate of the water/methanol mixture. If desired, the salts could be washed into a separate vacuum flask. 28 ml of chloroform was added to the water/methanol filtrate to create a 3.5:1 chloroform:methanol ratio. The water/methanol filtrate with the added chloroform was put in a separatory funnel and the product (compound V) was extracted into the chloroform:methanol. The water and organic solvents were allowed to separate and the organic layer was removed and filtered. The organic layer was evaporated under vacuum at 30° C. or less. The residue containing the product was dissolved in 2 ml of methanol and placed in an ice bath. O.2 ml of 1 M ethereal HCl was added to 1 ml of dry methanol and 1 ml of diethyl ether, which was then added to the cold 2 ml methanol in the ice bath, thereby forming the HCl salt of compound V. 30 ml of diethyl ether was added to the cold methanol to precipitate the product, 13-deoxydoxorubicin HCl (V). The precipitate was washed with diethyl ether to remove methanol, and was then dried in a dessicator under vacuum. Purity was measured by HPLC. The yields of product from the reactions, relative to doxorubicin HCl (IV), are shown below.

Recovery, purity, and yield of 13-deoxydoxorubicin HCl (V) synthesized from starting material compound III or compound II which were synthesized at various temperatures Synthesis Temperature of Starting Material

|  | Cold | | RT | | Hot | |
| --- | --- | --- | --- | --- | --- | --- |
| Compound | III | II | III | II | III | II |
| Recovery (%) | 84 | 53 | 61 | 51 | 63 | 49 |
| Purity (%) | 57 | 69 | 83 | 66 | 69 | 69 |
| Yield (%) | 48 | 37 | 51 | 34 | 43 | 34 |

The yield of compound V was consistently higher with compound III as the starting material compared to using compound II as the starting material, regardless of the temperature at which the starting material was synthesized. The average yield of compound V from the three compound III starting materials was 47.3%±2.3 (SE), which was 35% greater than the average yield from the three compound II starting materials, 35.0%±1.0 (SE), $p<0.05$. Similar experiments with compound VII synthesized under hot conditions produced a 34% yield of compound V. Experiments with compounds I and VI confirmed that a significant amount of these compounds were still present in the precipitated compound V product, giving poor purity and yield.

EXAMPLE 3

Preparation of 5-imino-13-deoxydoxorubicin HCl (VIII) from 13-benzene-sulfonylhydrazonedoxorubicin HCl (III)

Compound V was synthesized according to Example 1, starting with 200 mg of compound III. The reaction provided a 56.7% yield of crude compound V product, having 67.5% purity. 100 mg of this material was dissolved in 2 ml dry methanol and placed in an ice bath. 6 ml of 2M methanolic ammonia was added. The reaction mixture was maintained at 0-4° C. for four days. Thereafter, the methanol was evaporated under vacuum at 30° C. or less. To remove traces of ammonia, the residue was dissolved in 15 ml 4:1 chloroform:methanol and the solution evaporated. This was repeated twice. The residue was dissolved in 4 ml of dry methanol and the product, compound VIII, was precipitated by the addition of 60 ml of diethyl ether. The precipitate was washed with diethyl ether and dried under vacuum in a dessicator. There was an 81% recovery with 67% purity, providing an 80% yield.

It is generally known in the art that a strong acid is required in the reaction to reduce the 13-hydrazone anthracycline starting material, in the presence of cyanoborohydride. This is probably because the reaction is performed at relatively low temperatures (less than 100° C.), which is required to avoid breakdown of the 13-deoxy anthracycline product. The strong acid must be quenched or neutralized at the end of the reaction by adding base, or separated from the 13-deoxy anthracycline product by adding, for example, halocarbon solvent in order to prevent breakdown of the product. The purification of the final product would be greatly facilitated if the reaction mixture could be dried and then processed for purification on a preparative HPLC, or the reaction mixture applied directly to preparative HPLC. The presence of the strong acid appears to interfere with the separation of the product from the impurities during preparative HPLC, and produces a relatively low yield of pure product. Any attempt to dry the reaction mixture at the end of the reaction concentrates the strong acid and destroys the product.

In our search for a weak acid that would produce significant production of product, but not require neutralization or separation, we found that the pyridinium salt of p-toluenesulfonic acid was, surprisingly, effective in this regard. The reaction solution at the end of the reaction is stable at room temperature and the solvent can be removed to produce a stable dry residue. The residue can be stored for future workup, or it can be dissolved in suitable solvents for direct application to preparative HPLC purification. The reaction can be performed as described above, except that the reaction is performed, preferably, at about 65° C. to 75° C. for about 45 minutes, and the p-toluenesulfonic acid is replaced with pyridinium-p-toluenesulfonate, at about 66 mg per 100 mg of hydrazone starting material. Heretofore it has been unknown that acidic pyridinium salts would be useful in the reduction reaction of the present invention and provide these advantages.

EXAMPLE 4

Preparation of 13-deoxydoxorubicin HCl (V) from 13-benzenesulfonyl-hydrazonedoxorubicin HCl (III) Using pyridinium-p-toluenesulfonate in Place of p-toluenesulfonic Acid 100 mg of compound III was dissolved in 6 ml dry methanol with 100 mg of $NaCNBH_3$. The reaction mixture was placed in an ice bath. 66 mg of pyridinium-p-toluenesulfonate was dissolved in 2 ml dry methanol and was then added to the cold reaction mixture, providing a total of 8 ml methanol. The reaction mixture was then heated at about 72° C. for 45 minutes. At the end of 45 minutes the reaction mixture was cooled below 30° C. and 0.05 ml water was added to the reaction mixture to promote hydrolysis of the reduced hydrazone, producing the product, 13-deoxydoxorubicin HCl (V). HPLC analysis showed that there was a 55% yield of 13-deoxydoxorubicin HCl (V), relative to doxorubicin HCl (IV). This reaction mixture can be purified directly on preparative HPLC, the methanol can be removed and the residue dissolved in media suitable for chromatography, the reaction mixture can be neutralized and extracted as described above, and the reaction mixture can be used to form the 5-imino-13-deoxyanthracycline derivative by adding ammonia as described above.

The foregoing description has been limited to specific embodiments. It will be apparent, however, that variations and modifications may be made by those skilled in the art to the disclosed embodiments, with the attainment of some or all of its advantages and without departing from the spirit and scope of the present disclosure. For example, extractions of the water/methanol reaction mixture or the filtered salts can use solvent mixtures of halocarbons:alcohol ranging from 9:1 to 2:1. Various halocarbon solvents can be used besides chloroform, such as, for example, dichloromethane. Various alcohols can be used besides methanol, such as, for example, ethanol. Various ethers can be used besides diethyl ether, such as, for example, tertiary methyl butyl ether. Various acids can be used besides para-toluenesulfonic acid, such as, for example, HCl or camphorsulfonic acid. Methanolic HCl can be used in addition to ethereal HCl. Benzene- or para-substituted benzene-, sulfonylhydrazone aglycones can be used to produce 13-deoxy aglycones which can then be used to synthesize 13-deoxy anthracyclines by addition of a sugar. HCl salts can be formed before or after the synthesis of 5-imino-13-deoxy anthracyclines. 13-deoxy, or 5-imino-13-deoxy anthracyclines can be purified by chromatography before or after HCl salt formation. Substitutions on the benzene ring of the 13-benzenesulfonylhydrazone anthracycline can be ortho and meta as well as para. Other acidic pyridinium salts can be used besides pyridinium-p-toluenesulfonate.

It will be understood that various changes in the details, materials, and arrangements of the parts which have been described and illustrated above in order to explain the nature of this disclosure may be made by those skilled in the art without departing from the principle and scope as recited in the following claims.

What is claimed is:

1. A compound represented by the formula:

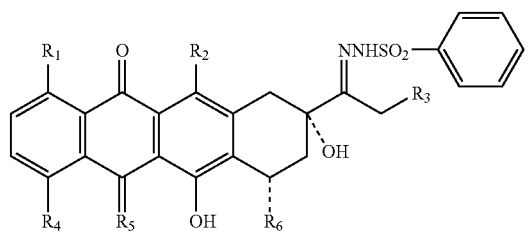

wherein:
$R_1$, $R_2$ and $R_3$ are H or OH;
$R_4$ is H, OH, alkyl, or O-alkyl;
$R_5$ is O or NH; and
$R_6$ is a sugar moiety
wherein the sugar moiety is

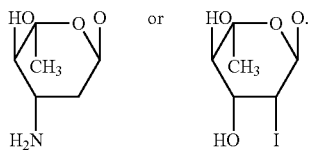

2. The compound of claim 1, wherein the compound is a derivative of an anthracycline selected from the group consisting of epirubicin, and annamycin.

3. A method for producing a compound according to claim 1 which comprises reacting a 13-keto anthracycline or acid salt thereof with benzene-sulfonylhydrazide in an alcohol solvent at about 35 to 50° C. for about 10 to 24 hours.

4. A process for preparing 13-deoxy anthracyclines, comprising:
1) forming an alcohol solution of a 13-benzene-, or substituted benzene-, sulfonylhydrazone anthracycline;
2) adding a reducing agent and an acidic pyridinium salt to the solution; and
3) heating the solution to reduce the 13-benzene-, or substituted benzene-, sulfonylhydrazone anthracycline,
wherein the acidic pyridinium salt is pyridinium p-toluenesulfonate and the reducing agent is sodium cyanoborohydride.

5. The process according to claim 4, further comprising the step of hydrolyzing the reduced 13-benzene-sulfonylhydrazone anthracycline, thereby forming the 13-deoxy anthracycline.

6. The process according to claim 4 wherein the heating is at about 65° C. to about 75° C.

7. The process according to claim 4 wherein the 13-benzene-sulfonylhydrazone anthracycline is a derivative of an anthracycline selected from the group consisting of epirubicin, and annamycin.

8. A process for preparing a 5-imino-13-deoxy anthracyclines, comprising:
1) preparing a 13-deoxy anthracycline according to claim 4; and
2) converting the 13-deoxy anthracycline to the corresponding 5-imino-13-deoxy anthracycline with ammonia at less than about 20° C.,
wherein the 13-deoxy anthracycline is synthesized from a corresponding 13-benzenesulfonylhydrazone anthracycline.

9. The process according to claim 8 wherein the step of converting the 13-deoxy anthracycline to the corresponding 5-imino-13-deoxy anthracycline with ammonia is at about 1° C. to about 4° C. for 1 to 4 days.

10. The process according to claim 8 wherein the 13-deoxy anthracycline is selected from the group consisting of the 13-deoxy forms of epirubicin, and annamycin.

11. The compound of claim 1, wherein $R_6$ is

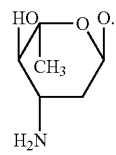

12. The compound of claim 1, wherein $R_6$ is

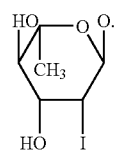

* * * * *